April 9, 1963 TAKEO YUGE ETAL Plant Pat. 2,248

AZALEA PLANT

Filed Feb. 20, 1961

INVENTORS

TAKEO YUGE
KANJI K. YUGE

BY Spensley and Horn
ATTORNEYS

United States Patent Office

Plant Pat. 2,248
Patented Apr. 9, 1963

2,248
AZALEA PLANT

Takeo Yuge and Kanji K. Yuge, both of
177 E. Mariposa St., Altadena, Calif.
Filed Feb. 20, 1961, Ser. No. 90,610
1 Claim. (Cl. 47—60)

This invention relates to a new and distinct variety of azalea plant characterized particularly by its early and extended blooming season and its bright red flowers with orange undertones which are produced profusely on a plant of fine, uniformly compact growth habit. The present variety commences blooming in September and is heavily in bloom in December in southern California without forcing or heating. Blooming continues through March with flowers that are long lasting with no fading or color change as the flowers age. Each of the flowers will last at least three weeks with each bud blossoming into two to five separate flowers.

This variety of azalea plant was produced in the experimental garden of the applicants' nursery at Altadena, California; the variety being the result of a cross between a Belgian semi-double unpatented variety known as Miss Cottage Gardens and a Belgian Indica azalea being a selected double seedling of the inventors known as Kaho, a variety which is unpatented. This cross pollination was carried out in the applicants' nursery at Altadena, California, in February 1950, the seeds resulting from the cross pollination were collected in November 1950 and planted in March 1951. The seedlings produced in this manner were observed over an extended period of time and this particular variety was selected and segregated.

Upon the cross being recognized as novel, and particularly when the extended and early blooming season of the variety was found, it was taken for propagation by cuttings at the aforesaid nursery in Altadena, California, and such cuttings produced azalea plants which carried forward all of the new and distinct features of the subject original plant. Subsequent propagation of the variety by cuttings further evidenced that the variety is fixed in its floricultural characteristics.

In the accompanying illustration:

Figure 1:
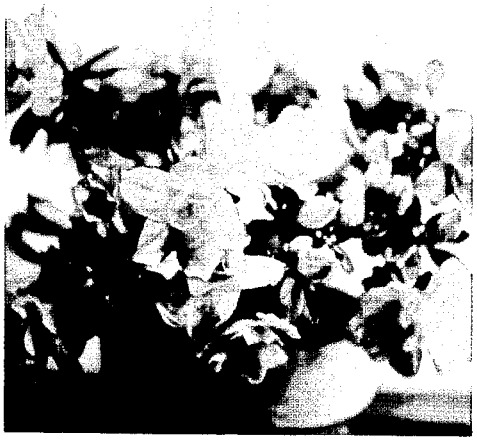
FIGURE 1 is a perspective view showing the flowers in bloom.
Figure 2:
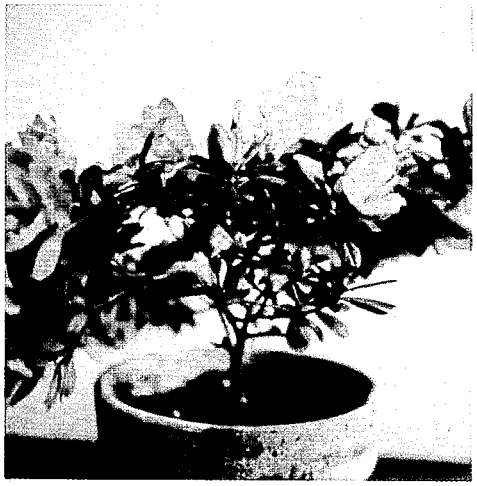
FIGURE 2 is a perspective view of a stem, with leaves and flowers.
Figure 3:
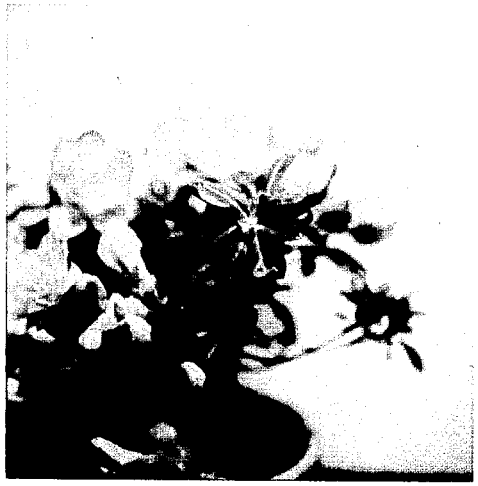

Referring now more specifically to the botanical details of the new and distinct variety of azalea plant of the present invention, the following is an outline description of the same:

*Plant*

Form: Many branched, rounded, symmetrical form.

Growing habit: Dense and bushy with heavy dark green foliage. The rate of growth is rapid and more rapid than most prior Belgian varieties.

Blooming habit: Flowers bloom out evenly over the entire plant when forced in the greenhouse or flowered naturally in the garden. Usually two to five separate flowers blossom from each bud produced on each stem.

Blooming season: September through March in southern

California without forcing or heating. The plant is heavily in bloom in southern California in December.

Foliage:

*Size.*—Mature foliage 1¼″ to 2″ long and ½″ to ⅝″ in width.

*Color.*—Dark green. (See chart below.)

*Shape.*—Oblong—elliptic; slightly mucronate tip.

*Aspect.*—Glossy with some hairs on both sides. Slightly pubescent.

*Texture.*—Medium.

*Edges.*—Slight serrations and hairs.

*Ribs and veins.*—Pinnately veined. Six veins leading off main center vein, three to four very short veins leading off main center vein at top of leaf.

*Flower*

Size: Average 2½″ in diameter by 2″ in length.

Borne: Two to five to each stem.

Stem: Medium length with sufficient strength to hold the flowers properly.

Form: Semi-double, ruffled petals.

Permanence: Long lasting without fading or changing of color as flowers age. Flowers last average of at least three weeks in southern California.

Petalage: Five to six outer petals with eight to nine inner petals.

Color: Bright salmon-red. (See chart below.)

Petals:

*Texture.*—Medium to heavy.

*Appearance.*—Velvety with edges ruffled.

*Shape.*—Broadly ovate, not pointed, tapering abruptly at lower end.

*Arrangement.*—Coalesced at base. The lower part of each petal is grown together with the lower part of the next petal.

*Persistence.*—Remains firm without wilting or color change until flower falls.

Reproductive organs: Has variable reproductive organs.

*Stamens.*—0 to five (5). Same color as flower.

*Pollen.*—Black.

*Ovaries.*—Normal.

The color designations according to "A Dictionary of Color" by Maerz and Paul are as follows:

| Part | Color | Plate | Letter | Number |
|---|---|---|---|---|
| Foliage: | | | | |
| New Leaves | Peridot | 22 | L | 6 |
| Mature Leaves | Brunswick Green | 23 | C | 12 |
| Stems (New Growth) | Kazak Coptic | 7 | L | 9 |
| Flower: | | | | |
| Outer Edge of Petals | Sultan | 4 | K | 6 |
| Base of Petals | Red Cross | 4 | L | 6 |

Having thus disclosed our invention, we claim:

The new and distinct variety of azalea plant substantially as herein shown and described being a cross between a Belgian semi-double variety known as Miss Cottage Gardens and a Belgian double, Kaho, and characterized by its early and extended blooming season.

No references cited.